United States Patent [19]

Zahn et al.

[11] Patent Number: 5,502,206
[45] Date of Patent: Mar. 26, 1996

[54] LIQUID-CRYSTALLINE ORGANOSILOXANES CONTAINING CHIRAL TARTARIMIDES

[75] Inventors: Ingo P. Zahn, München; Franz-Heinrich Kreuzer, Martinsried; Hans-Peter Weitzel, Reischach, all of Germany

[73] Assignee: Consortium für elektrochemische Industrie GmbH, Munich, Germany

[21] Appl. No.: 239,780

[22] Filed: May 9, 1994

[30] Foreign Application Priority Data

May 27, 1993 [DE] Germany ............... 43 17 704.2

[51] Int. Cl.$^6$ ............... C07D 207/416; C07F 7/21
[52] U.S. Cl. ............... 548/406; 548/544; 548/547; 528/28
[58] Field of Search ............... 548/406, 544, 548/547

[56] References Cited

U.S. PATENT DOCUMENTS

| | | | |
|---|---|---|---|
| 3,586,699 | 6/1971 | Wu | 260/326.5 |
| 4,996,330 | 2/1991 | Scherowsky et al. | 548/544 |
| 5,211,877 | 5/1993 | Andrejewski et al. | 252/299.1 |
| 5,221,759 | 6/1993 | Haeberle et al. | 556/413 |
| 5,304,667 | 4/1994 | Haeberle et al. | 556/413 |

FOREIGN PATENT DOCUMENTS

| | | |
|---|---|---|
| 0446912 | 9/1991 | European Pat. Off. . |
| 0466183 | 1/1992 | European Pat. Off. . |
| 0358208 | 3/1994 | European Pat. Off. . |
| 3822121 | 3/1990 | Germany . |

OTHER PUBLICATIONS

Derwent Abstract, AN 91–275546/38, zu EP 446 912, (1991).

Makromol. Chem. 179, 829–832 (1978), "Synthesis of Cholesteric Liquid Crystalline Polymers", H. Finkelmann et al.

W. Noll, Chemistry and Technology of Silicones; S. 191–239, 1989.

Primary Examiner—David B. Springer
Attorney, Agent, or Firm—Martin Connaughton

[57] ABSTRACT

The liquid-crystalline organosiloxanes containing, per molecule, at least one Si—C-bonded chiral tartarimide radical of the formula $$\text{M-N} \underset{\underset{O}{\|}}{\overset{\overset{O}{\|}}{\underset{C}{\diagdown}}} \underset{C}{\overset{C}{\diagup}} \underset{\underset{O}{\|}}{\overset{O-C-M-A^5_k}{}} \quad (1)$$

in which M, $A^5$ and k are as defined in claim 1, can be employed as chiral filter materials, for decorative purposes and in optical elements.

7 Claims, No Drawings

LIQUID-CRYSTALLINE ORGANOSILOXANES CONTAINING CHIRAL TARTARIMIDES

FIELD OF INVENTION

The present invention relates to liquid-crystalline organosiloxanes containing chiral tartarimides, to a process for their preparation, to their use, to organosilanes which can be condensed to form liquid-crystalline organosiloxanes containing chiral tartarimides, to chiral tartarimides, and to mixtures of liquid-crystalline organosiloxanes containing chiral tartarimides with other liquid-crystalline materials.

BACKGROUND OF INVENTION

Twisted liquid-crystal materials generally have smectic, nematic or cholesteric phases. Liquid-crystal mixtures frequently contain one or more optically active components in order to induce a chiral structure. For example, cholesteric liquid crystals can comprise a nematic base material and one or more optically active dopes, which produce either a right-handed or left-handed twist in the nematic material. Cholesteric liquid crystals reflect light in a wavelength range for which the wavelength is approximately equal to the helix pitch ($\lambda = n \cdot p$). The reflected light is fully circular-polarized. The direction of rotation of the reflected light depends on the directional rotation of the cholesteric helix structure. The light circular-polarized in the opposite direction in each case is transmitted at the same strength.

A large number of optically active dopes which are more or less suitable for certain purposes are described in the literature. U.S. Pat. No. 4,996,330 discloses chiral N-substituted tartarimides which are diesterified at the hydroxyl groups by mesogenic radicals. Such substances can be used as additives in electro-optical display devices, such as TN or STN cells, in order to achieve the requisite twist.

Polymeric or crosslinked cholesteric liquid crystals enable more extensive applications. They can be used to prepare LC pigments having novel effects or reflective polarizing filters, inter alia. The incorporation of methacrylates of cholesterol or derivatives thereof as dopes into liquid-crystalline polymers is described by H. Finkelmann, H. Ringsdorf et al., in Makromol. Chem. 179, 829–832 (1978).

EP-A-358 208 describes cyclic siloxanes containing mesogenic side groups, in which some of the side groups have been esterified by methacrylic acid. These siloxanes can therefore also be crosslinked. The dopes incorporated into these polymers are hydrosilylated allyloxybenzoates of cholesterol or derivatives thereof. However, they have only a relatively low helical twisting power (abbreviated to HTP) and must therefore be added in large amounts (about 50%) in order to cause color effects in the visible region. The large amount of dopes means that the crosslinker group density cannot be chosen to be very high. In addition, the chiral dopes are relatively expensive.

For the construction of some optical filters, a large spectral width of the reflection light is of crucial importance. The spectral width of the reflection light can be increased by a high proportion of aromatic compounds in the liquid crystal. However, cholesterol-containing systems have a high content of cyclohexyl rings. The spectral width of the reflection light is thus frequently too small for these applications.

For some applications of optical filters, it would furthermore be desirable to reflect circular-polarized light of both directions of rotation. The above mentioned cholesterol-containing systems generally likewise do not offer this possibility.

SUMMARY OF INVENTION

The object of the present invention was to provide liquid-crystalline organosiloxanes which, instead of cholesterol derivatives, contain more suitable chiral compounds having a high HTP, are capable of forming cholesteric phases, if desired reflect circular-polarized light of both directions of rotation and can be cross-linked if required.

The present invention relates to liquid-crystalline organosiloxanes which contain, per molecule, at least one Si—C-bonded, chiral tartarimide radical of the formula

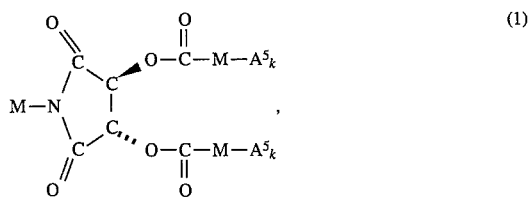

in which

M is a radical of the formula

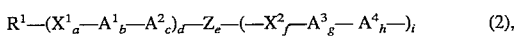

where, in the above formulas 1 and 2, $R^1$ is a radical of the formula $C_nH_m$, in which is an integer having a value of from 0 to 20, m has the value $2n$ or, if n is at least 2, can also have the value $(2n-2)$, and one or more methylene units in $R^1$ can be replaced by oxygen atoms, which can be bonded to carbon and/or silicon atoms, $X^1$ and $X^2$ are identical or different divalent radicals chosen from the group consisting of —O—, —COO—, —CONH—, —CO—, —S—, —C≡C—, —CH=CH—, —CH=N—, —CH$_2$—, —N=N— and —N=N(O)—, $A^1$, $A^2$, $A^3$ and $A^4$ are identical or different divalent radicals, namely 1,4-phenylene, 1,4-cyclohexylene, substituted arylenes having 1 to 10 carbon atoms, substituted cycloalkylenes having 1 to 10 carbon atoms and heteroarylenes having 1 to 10 carbon atoms, Z are identical or different divalent to tetravalent benzene, cyclohexane or cyclopentane radicals, $A^5$ are identical or different, saturated or olefinically unsaturated alkyl, alkoxy or cycloalkyl radicals, each having 1 to 16 carbon atoms, cholestane radicals, cholesteryl radicals, halogen atoms, hydrogen atoms, hydroxyl, nitrile, acryloxy, (meth)-acryloxy, (meth-)acryloxyethyleneoxy, (meth)acryloxydi(ethyleneoxy), (meth)acryloxytri(ethyleneoxy), R- or S-tetrahydrofurancarboxylate and trialkylsiloxy groups whose alkyl radicals each have 1 to 8 carbon atoms, a, b, c, d, f, g, h, i and k are each identical or different integers having a value of from 0 to 3, where the sum a+b+c+d+e+f+g+h+i+k is at least 2 and the sum of d and i is at most 4, and e is a number having a value of 0 to 1.

The liquid-crystalline organosiloxanes according to the invention have a significantly greater HTP and thus a better optical rotatory power than the cholesterol-containing liquid-crystalline organosiloxanes, and therefore considerably smaller amounts of chiral tartarimide radicals of formula 1 need to be employed as dope in order to achieve the same optical effect, in order to achieve the same reflection wavelength.

The cholesteric phase can, after alignment above the glass transition temperature, be preserved by quenching to give the glass state and is stable at room temperature.

In addition to chiral tartarimide radicals, the liquid-crystalline organosiloxanes preferably also contain other mesogenic radicals which enable subsequent free-radical or ionic crosslinking.

By modifying the content of chiral tartarimide radicals and the ratio between chiral tartarimide radicals and other mesogenic radicals in the liquid-crystalline organosiloxanes according to the invention, the reflection wavelength of the selective reflection can be adjusted. Owing to the large HTP values, only a proportion of from 10 to 20 mole %, based on all mesogenic radicals present in the organosiloxanes, of chiral tartarimide radicals is required in order to obtain a reflection in the visible region, whereas between 40 and 50 mole % of cholesteryl radicals are required in the case of the corresponding cholesterol-containing organosiloxanes.

The liquid-crystalline organosiloxanes according to the invention are preferably built up from at least two units of the formula $$[B_oR_pH_qSiO_{(4-o-p-q)/2}] \quad (3),$$

in which

B is a radical of formula 1, and, if desired, a radical of the formula $$M—A^5k \quad (4),$$

where, in the above formulas 3 and 4,

R are identical or different, substituted or unsubstituted $C_1$- to $C_{18}$-hydrocarbon radicals, o is an integer having a value of from 0 to 3, p is an integer having a value of from 0 to 3 and a mean value of from 0.8 to 2.2, q is an integer having a value of from 0 to 3, and the sum of o, p and q is at most 3, and M, $A^5$ and k are as defined for the above formula 1.

It is frequently desired, for application reasons, that the mesogenic groups of formula 4 contain polar functions, such as the nitrile group, in order to achieve a high dielectric anisotropy effect in the liquid crystal.

Examples of unsubstituted radicals R are alkyl radicals, such as the methyl, ethyl, n-propyl, isopropyl, n-butyl, iso-butyl, tert-butyl, n-pentyl, iso-pentyl, neopentyl and tert-pentyl radicals, hexyl radicals, such as the n-hexyl radical, heptyl radicals, such as the n-heptyl radical, octyl radicals, such as the n-octyl radical, and isooctyl radicals, such as the 2,2,4-trimethylpentyl radical, nonyl radicals, such as the n-nonyl radical, decyl radicals, such as the n-decyl radical, dodecyl radicals, such as the n-dodecyl radical, and octadecyl radicals, such as the n-octadecyl radical; alkenyl radicals, such as the vinyl and allyl radicals; cycloalkyl radicals, such as cyclopentyl, cyclohexyl, cycloheptyl and methylcyclohexyl radicals; aryl radicals, such as the phenyl, naphthyl, anthryl and phenanthryl radicals; alkaryl radicals, such as o-, m- and p-tolyl radicals, xylyl radicals and ethylphenyl radicals; and aralkyl radicals, such as the benzyl radical and the α- and β-phenylethyl radicals.

Examples of substituted radicals R are cyanoalkyl radicals, such as the β-cyanoethyl radical, and halogenated hydrocarbon radicals, for example haloalkyl radicals, such as the 3,3,3 -tri-fluoro-n-propyl radical, the 2,2,2,2',2',2'-hexafluoroisopropyl radical, and the heptafluoroisopropyl radical, and haloaryl radicals, such as the o-, m- and p-chlorophenyl radicals.

R is preferably in each case a halogenated or unhalogenated hydrocarbon radical having 1 to 18, in particular 1 to 10, carbon atoms.

Particularly preferred radicals R and $C_1$- to $C_4$-alkyl radicals and phenyl radicals, in particular methyl radicals.

The radicals $X^1$ and $X^2$ can, if they do not have a symmetrical structure, be bonded to each of their binding partners at each of their ends. In the above formulas 3 and 4 and in the formulas below, the radical —COO— and —OOC—, the radical —CONH— and —NHCO—, and the radical —CH=N— and —N=CH— can be bonded in this way.

Preferred substituents for the substituted arylenes and cycloalkylenes $A^1$, $A^2$, $A^3$ and $A^4$ are halogen atoms, $C_1$- to $C_4$-alkoxy radicals, nitro and cyano groups, $C_1$- to $C_6$-alkyl radicals, carboxy($C_1$- to $C_4$-alkyl) radicals and tri($C_1$- to $C_4$-alkyl)siloxy radicals.

In $R^1$, n preferably has a value of from 3 to 6, and m preferably has the value 2n.

Examples of radicals $A^5$ are alkyl radicals, such as the methyl, ethyl, n-propyl, isopropyl, n-butyl, isobutyl, tert-butyl, n-pentyl, isopentyl, neopentyl and tert-pentyl radicals, hexyl radicals, such as the n-hexyl radical, heptyl radicals, such as the n-heptyl radical, octyl radicals, such as the n-octyl radical and isooctyl radicals, such as the 2,2,4-trimethylpentyl radical, nonyl radicals, such as the n-nonyl radical, decyl radicals, such as the n-decyl radical, dodecyl radicals, such as the n-dodecyl radical, and hexadecyl radicals, such as the n-hexadecyl radical; alkenyl radicals, such as the vinyl and allyl radicals, butenyl, pentenyl, hexenyl, heptenyl, octenyl, octadienyl, decenyl, dodecenyl and hexadecenyl radicals; cycloalkyl radicals, such as cyclopentyl, cyclohexyl, cycloheptyl and methyl-cyclohexyl radicals; alkoxy radicals, such as the methoxy, ethoxy, n-propoxy, isopropoxy, n-, sec- and tert-butoxy, pentoxy, hexoxy, octoxy, decoxy and hexadecoxy radicals; alkenoxy radicals, such as the allyloxy radical, butenyloxy, pentenyloxy, hexenyloxy, octenyloxy, decenyloxy and hexadecenyloxy radicals; cycloalkyl radicals, such as the cyclopentyl, cyclohexyl and cycloheptyl radicals; cycloalkenyl radicals, such as cyclopentenyl, cyclohexenyl and cycloheptenyl radicals; cholestane radicals; the cholesteryl radical; fluorine, chlorine or bromine atoms; hydrogen atoms; and hydroxyl, nitrile, trimethylsilyl and triethylsilyl groups.

It is particularly preferred that $—R^1—(X^1_a—A^1_b—A^2_c)_d—$ in the above formula 2 is a radical of the formula

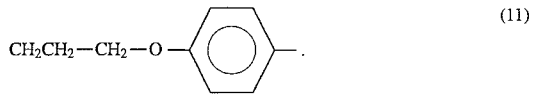
(11)

Particularly preferred compounds of the formula 4 are those of the formula

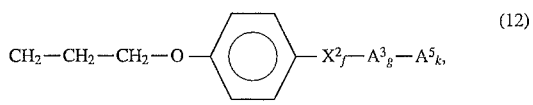
(12)

in which $X^2$, $A^3$, $A^5$, f, g and k are as defined for the formula 4, and f preferably has the value 1, g is preferably either 0 or 1, and k preferably has the value 1.

It is particularly preferred that the chiral tartarimide radicals have the formula

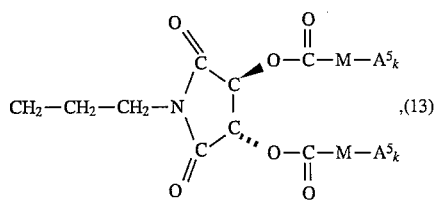

(13)

in which M, A⁵ and k are as defined for formula 1.

The liquid-crystalline organosiloxanes according to the invention can be prepared by reacting organosiloxanes and/or organosilanes which can be condensed to form organosiloxanes with alkenes or alkynes containing mesogenic groups of formula 1 and, if desired, of formula 4, where the organosiloxanes and at least some of the organosilanes contain at least one hydrogen atom bonded directly to silicon.

In a preferred process for the preparation of liquid-crystalline organosiloxanes of formula 3, in which n in the radicals of formula 2 is an integer having a value of from 2 to 20, organosiloxanes built up from units of the formula $$[R_p H_{q+o} SiO_{(4-o-p-q)/2}] \tag{14}$$

and/or organosilanes of the formula $$R_r H_{s+o} SiY_{(4-o-r-s)/2} \tag{15},$$

are reacted with compounds of the formula

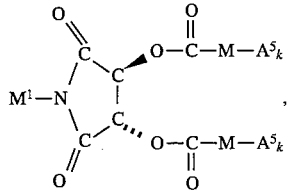

(16)

and, if desired, compounds of the formula $$R^2\text{—}(X^1{}_a\text{—}A^1{}_b\text{—}A^2{}_c)_d\text{—}Z_e\text{—}(\text{—}X^2{}_f\text{—}A^3{}_g\text{—}A^4{}_h\text{—})_i\text{—}A^5{}_k \tag{17},$$

and, if organosilanes of formula 15 are employed, the resultant organosilanes of the formula $$B_o R_r H_s SiY_{(4-o-r-s)/2} \tag{18},$$

are condensed, where, in the above formulas 14 to 18,

M¹ is a radical of the formula $$R^2\text{—}(X^1{}_a\text{—}A^1{}_b\text{—}A^2{}_c)_d\text{—}Z_e\text{—}(\text{—}X^2{}_f\text{—}A^3{}_g\text{—}A^4{}_h\text{—})_i \tag{19},$$

Y is a condensable group,

R² is a radical of the formula $C_n H_m{}^1$, in which m¹ has the value 2n−1 or 2n−3, and r and s are each an integer having a value of from 0 to 3, the sum of o, r and s is at most 3, and o, p, q, M, X¹, X², A¹, A², A³, A⁴, A⁵, a, b, c, d, e, f, g, h, i, k, Z, B and R are as defined in claims 1 and 2.

Preferably Y is a halogen atom or a C₁- to C₄-alkoxy group, in particular a chlorine atom or a methoxy or ethoxy group. The value of s is preferably 0 or 1.

In the above formulas 16 and 17, n in R² preferably has a value of from 3 to 6, in particular 3, and m preferably has the value 2n−1.

Particularly preferred compounds of formula 17 are those of formula

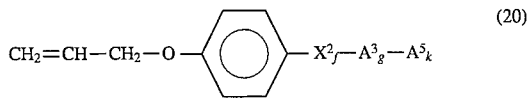

(20)

in which X², A³, A⁵, f, g and k are as defined for formula 4, and f preferably has the value 1, g is preferably 0 or 1, and k preferably has the value of 1.

Particularly preferred compounds of formula 16 are those of the formula

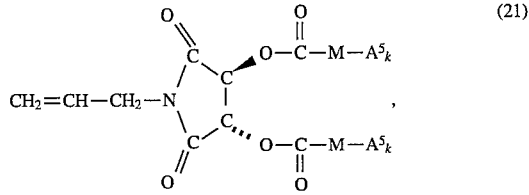

(21)

in which M, A⁵ and k are as defined for formula 1.

The compounds of formula 21 can be hydrosilylated at hydrogen atoms bonded directly to silicon, during which virtually no undesired side reactions occur. Corresponding allyloxy esters otherwise have a high tendency toward isomerization of the double bond and subsequent elimination of propene. This is described, for example, in EP-A-466 183.

Preferred siloxanes of formula (14) are those in which at least 90% of the units are those of the following formulas 5 to 10,

| [(CH₃)₂SiO] | (5), |
|---|---|
| [(CH₃)HSiO] | (6), |
| [H₂SiO] | (7), |
| [H(CH₃)₂SiO₁/₂] | (8), |
| [(CH₃)₃SiO₁/₂] | (9), |
| and | |
| [HSiO₃/₂] | (10), | which contain from 2 to 100 silicon atoms per molecule, in particular from 2 to 15 silicon atoms per molecule. Particular preference is given to cyclic siloxanes built up from units of formula 6 and, if desired, formula 5.

The reaction of organosiloxanes and/or organosilanes which can be condensed to form organosiloxanes, containing hydrogen atoms bonded directly to silicon, with alkenes or alkynes of formulas 16 and 17 is carried out for example, by hydrosilylation in solvents, such as hydrocarbons, ethers or esters, with metals or compounds of the platinum group as catalysts. Suitable hydrosilylation processes are described, for example, in EP-A-466 183.

Liquid-crystalline organosiloxanes according to the invention containing methacryloxy and/or acryloxy groups in the mesogenic radicals of formula 4 are preferably prepared by the process described in EP-A-358 208.

From 0.1 to 10 mole, in particular from 0.5 to 2 mole, of the compounds of formulas 3 and 4 are preferably employed in the hydrosilylation per gram-atom of hydrogen atoms bonded directly to silicon atoms.

If organosiloxanes, for example of formula 15, are employed in the above process, these are condensed together with organosilanes or organosiloxanes containing chiral tartarimide radicals of formula 1 by known processes to give liquid-crystalline organosiloxanes. This can be carried out, inter alia, by reaction with acids, such as aqueous hydrochloric acid. Processes of this type are described in W. Noll: Chemistry and Technology of Silicones, Academic Press, Orlando, Fla., 1968, pages 191 to 239.

The above-described reactions give a mixture of different molecules.

The invention also relates to the alkenetartarimides of formula 16 above, which are intermediates in the preparation of the liquid-crystalline organosiloxanes.

The synthesis of the alkenetartarimides can be carried out, for example, by the following processes:

1. In the first step, a chiral tartaric anhydride is prepared by reaction of three equivalents of an acid chloride with tartaric acid according to the description in JACS 1933, 55, 2605, and is subsequently reacted with alkenamines at temperatures between 120° C. and 160° C. in suitable inert solvents, such as toluene.

2. In the first step, an alkenetartarimide is prepared by heating tartaric acid in the presence of stoichiometric amounts of alkenamine. The two OH groups which are still free are subsequently esterified by means of carboxylic acids or carboxylic acid chlorides by known processes. An example of such a process is described in U.S. Pat. No. 4,996,330.

The novel organosilanes of formula 18 above, in which o is an integer having a value of 1, 2 or 3, are likewise a subject-matter of the present invention as intermediates for the preparation of the liquid-crystalline organosiloxanes.

The liquid-crystalline organosiloxanes according to the invention can be used in various ways in optical elements, for decorative purposes and as polarizing colored filters, in particular notch filters. They allow the component of light which is polarized in a right-handed or left-handed manner to be reflected in certain prespecified spectral regions.

For the above application, both mixtures of the organosiloxanes according to the invention with one another and mixtures of the organosiloxanes according to the invention with other liquid-crystalline materials or pure organosiloxanes containing tartarimide radicals can be used. In particular, mixtures with other liquid-crystalline substances can also be used, allowing tuning of the reflection wavelength between 400 nm right-handed helix via infra-red right-handed helix, nematic (=infinite pitch), infrared left-handed helix to 400 nm left-handed helix.

The mixtures of the liquid-crystalline organosiloxanes with one another and with other liquid-crystalline materials are likewise a subject-matter of the present invention. Other constituents of such mixtures can be, for example, monomeric liquid-crystalline methacrylates and/or acrylates. The liquid-crystalline mixtures of methacryloxy and/or acryloxy group-containing components can be polymerized by known processes and also crosslinked if suitable components are selected.

The liquid-crystalline organosiloxanes according to the invention containing methacryloxy and/or acryloxy groups in the mesogenic radicals of formula 4 can be three-dimensionally crosslinked. This crosslinking is preferably effected by means of free radicals generated by peroxides, by UV light or by higher-energy electromagnetic radiation other than UV light, or thermally. The crosslinking can also be effected by means of crosslinking agents containing hydrogen atoms bonded directly to silicon atoms, with catalysis by the above mentioned platinum metal catalysts. It can also be carried out cationically or anionically. Particular preference is given to crosslinking by UV light. This crosslinking is described in EP-A-358 208.

In the examples below, unless otherwise stated, a. all amounts are by weight;

b. all pressures are 0.10 mPa (abs.);

c. all temperatures are 20° C.;

d. HTP—helical twisting power.

Preparation of the Alkenetartarimides

The alkenetartarimides 1a to 1d below were prepared by processes 1 and 2 described above and converted into liquid-crystalline organosiloxanes with other olefin-containing mesogenic compounds.

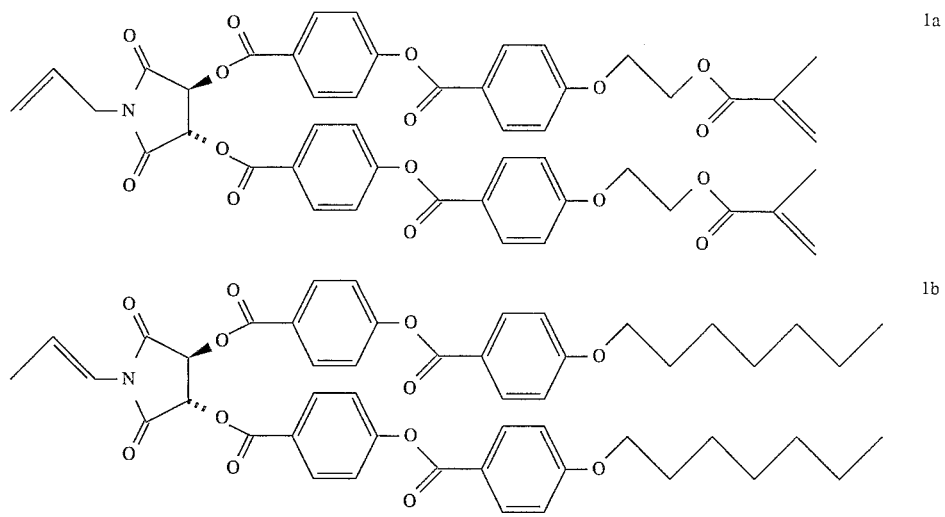

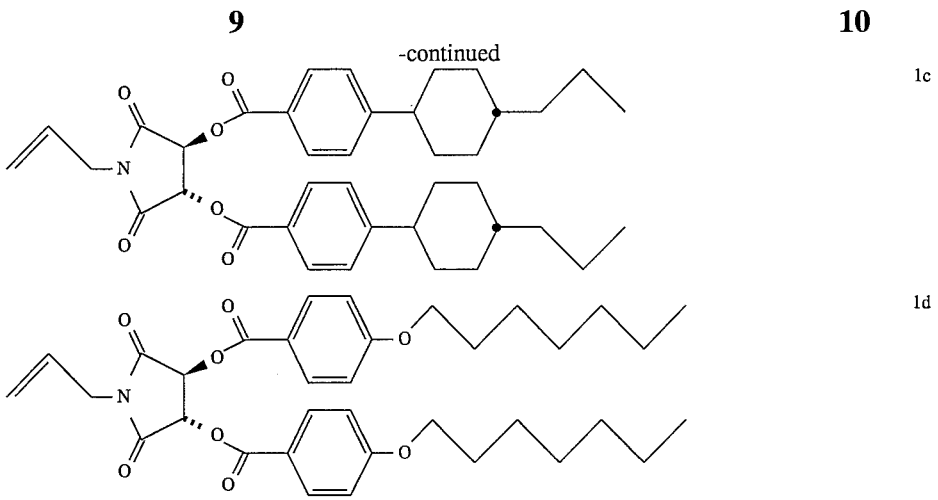

1c

1d

Preparation of (3R,4R)-(+)-allyl-3,4-bis[4-(trans-n-propylcyclohexyl)benzoyloxy] succinimide (alkenetartarimide 1c) by process 2 described above.

a. Preparation of the allylimide—200 g (1.33 mole) of L-(+)-tartaric acid and 76 g (1.33 mole) of allylamine were dissolved in 70 ml of hot water and heated at 140° C. for about 9 hours. The water formed during this time was removed by distillation. The intensely colored product was recrystallized from ethanol, giving 48.4 g (21% of theory) of colorless crystals.

b. Esterification of the allylimide—24.6 g (0.10 mole) of (4 -trans-n-propylcyclohexyl)-4-benzoic acid, 17.5 g (0.15 mole) of thionyl chloride and a few drops of DMF were stirred for 3.5 hours at 60° C. in 50 ml of toluene. The excess thionyl chloride and toluene were then removed by vacuum distillation.

The acid chloride attained in this way was taken up in 50 ml of toluene and added dropwise to a mixture of 8.56 g (0.05 mole) of allylimide, 15.2 g (0.15 mole) of triethylamine, a spatula tip of 4-dimethylaminopyridine and 150 ml of toluene at 10° C.

After the reaction mixture had been stirred for 18 hours, it was extracted by shaking first with 1N HCl, then with NaHCO₃ solution and H₂O. After the extract had been dried, the solvent was evaporated, giving 25.7 g (82% of theory) of product.

EXAMPLE 1

1.0 g (1.6 mmol) of (3R,4R)-(+)-allyl-3,4-bis[4-(trans-n-propylcyclohexyl)benzoyloxy] succinimide (alkenetartarimide 1c), 3.2 g (8.0 mmol) of 4-(4-methoxyphenyl)-phenyl 4 -(propen-2-oxy)benzoate and 0.96 g (3.2 mmol) of pentamethylcyclopentasiloxane were dissolved in 40 ml of toluene with gentle warming. 0.1 ml of catalyst solution (1% by weight of dicyclopentadienylplatinum dichloride in methylene chloride) was added, and the solution was stirred at 100° C. for one hour. The solution was cooled to below 50° C., 10 mg of aluminum salt of N-nitrosophenylhydroxylamine and 2.16 g (6.4 mmol) of 4-methacryloxyphenyl 4-(propen-2-oxy)benzoate dissolved in 20 ml of toluene were added, and the mixture was stirred at 70° C. for one hour. The resultant crude product was filtered through a short silica gel-filled column (l=3 cm, d=3 cm) in order to remove the catalyst, and was evaporated on a rotary evaporator, giving 4.76 g (65% of theory) of a substance having a reflection wavelength of 660 nm; the material had a glass transition temperature of −14° C. and a cholesteric phase up to the clearing point of 145° C. and had the following formula:

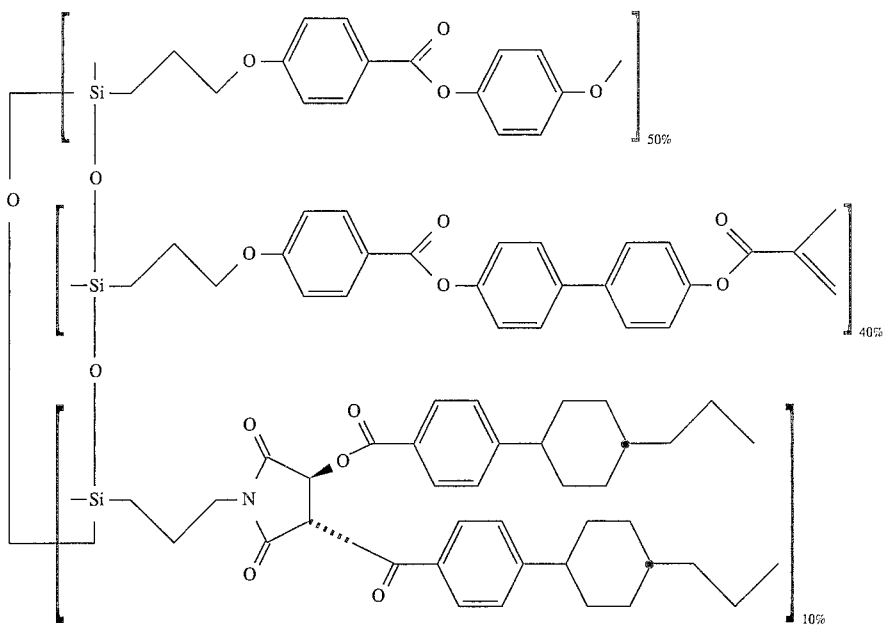

COMPARATIVE EXAMPLE 1

Analogously to Example 1, the following liquid-crystalline polyorganosiloxane was prepared using cholesterol as the chiral compound.

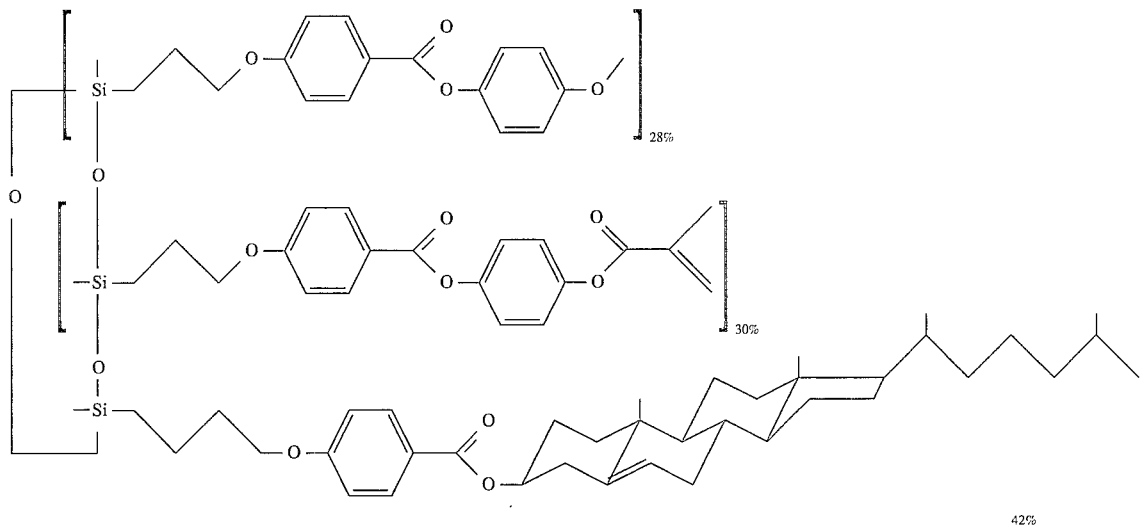

The reflection wavelength is again 660 nm here. However, more than four times the amount of chiral compound is required to achieve this.

EXAMPLE 2

1.0 g (1.6 mmol) of (3R,4R)-(+)-allyl-3,4-bis[4 -(trans-n-propylcyclohexyl)benzoyloxy]succinimide (alkenetartarimide 1c), 1.93 g (4.8 mmol) of 4-(4-methoxyphenyl)phenyl 4 -(propen-2-oxy)benzoate and 0.64 g (2.1 mmol) of pentamethylcyclopentasiloxane were dissolved in 40 ml of toluene with gentle warming. 0.1 ml of catalyst solution (1% by weight of dicyclopentadienylplatinum dichloride in methylene chloride) was added, and the solution was stirred at 100° C. for one hour. The solution was cooled to below 50° C., 10 mg of aluminum salt of N-nitrosophenylhydroxylamine and 1.44 g (4.25 mmol) of 4-methacryloxyphenyl 4-(propen-2-oxy)benzoate dissolved in 20 ml of toluene were added, and the mixture was stirred at 70° C. for one hour. The resultant crude product was filtered through a short silica gel-filled column (l=3 cm, d=3 cm) in order to remove the catalyst, and was evaporated on a rotary evaporator, giving 3.1 g (62%) of a substance having a reflection wavelength of 540 nm; the material had a glass transition temperature of −20° C. and a cholesteric phase up to the clearing point of 145° C.

EXAMPLE 3

0.5 g (0.8 mmol) of (3R,4R)-(+)-allyl-3,4-bis[4-(trans-n-propylcyclohexyl)benzoyloxy] succinimide (alkenetartarimide 1c), 1.6 g (4.0 mmol) of 4-(4-methoxyphenyl)-phenyl 4-(propen-2-oxy)benzoate, 0.9 g (3.2 mmol) of 4-(propen-2-oxy)-4-ethoxyazobenzene and 0.48 g (1.6 mmol) of pentamethylcyclopentasiloxane was dissolved in 30 ml of toluene with gentle warming. 0.1 ml of catalyst solution (1% by weight of dicyclopentadienylplatinum dichloride in methylene chloride) was added, and the solution was stirred at 100° C. for three hours. The resultant crude product was filtered through a short silica gel-filled column (l=3 cm, d=3 cm) in order to remove the catalyst, and reprecipitated twice from toluene in ethanol, giving 2.1 g (60%) of a substance having a reflection wavelength of 840 nm; the material had a glass transition temperature of O° C. and a cholesteric phase up to the clearing point of 120° C.

EXAMPLE 4

870 mg (1.39 mmol) of (3R,4R)-(+)-allyl-3,4-bis[4-(trans-n-propylcyclohexyl)benzoyloxy] succinimide, 1.48 g (5.2 mmol) of 4-(4-methoxyphenyl)-phenyl 4-(propen-2-oxy) benzoate, 2.5 g (6.6 mmol) of 4-(4-trans-n-propylcyclohexyl)phenyl 4-(propen- 2-oxy)benzoate and 833 mg (2.77 mmol) of pentamethylcyclopentasiloxane were dissolved in 15 ml of toluene with gentle warming. 0.05 ml of catalyst solution (0.5% by weight of dicyclopentadienylplatinum dichloride in methylene chloride) was added, and the solution was refluxed for 4 hours. The toluene solution of the reaction product was subsequently added dropwise to petroleum ether for further purification, giving 4.5 g (80% of theory) of a substance having a reflection wavelength of 610 nm; the material had a glass transition temperature of 9° C. and a cholesteric phase up to the clearing point of 125° C. and had the following formula

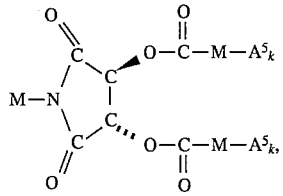
(1)

in which

M is a radical of the formula

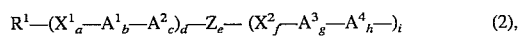
(2), where, in the above formulas 1 and 2, $R^1$ is a radical of the formula $C_nH_m$, in which n is an integer having a value of from 0 to 20, m has the value 2n or, if n is at least 2, can also have the value (2n–2), and one or more methylene units in $R^1$ can be replaced by oxygen atoms, which can be bonded to carbon and/or silicon atoms, $X^1$ and $X^2$ are identical or different divalent radicals from the group consisting of —O—, —COO—, —CONH—, —CO—, —S—, —C≡C—, —CH=CH—, —CH=N—, —CH$_2$—, —N=N— and —N=N(O)—, $A^1$, $A^2$, $A^3$ and $A^4$ are identical or different divalent radicals, selected from the group, consisting of 1,4-phenylene, 1,4-cyclohexylene, substituted arylenes having 6 to 10 carbon atoms, and substituted cycloalkylene, having 6 to 10 carbon atoms, where the substituents are selected from the group consisting of halogen atoms, $C_1$- to $C_4$-alkoxy radicals, nitro and cyano groups, $C_1$- to $C_6$-alkyl radicals, carboxy($C_1$- to $C_4$-alkyl) radicals and tri($C_1$- to $C_4$-alkyl)siloxy radicals, Z are identical or different divalent to tetravalent benzene, cyclohexane or cyclopentane radicals,

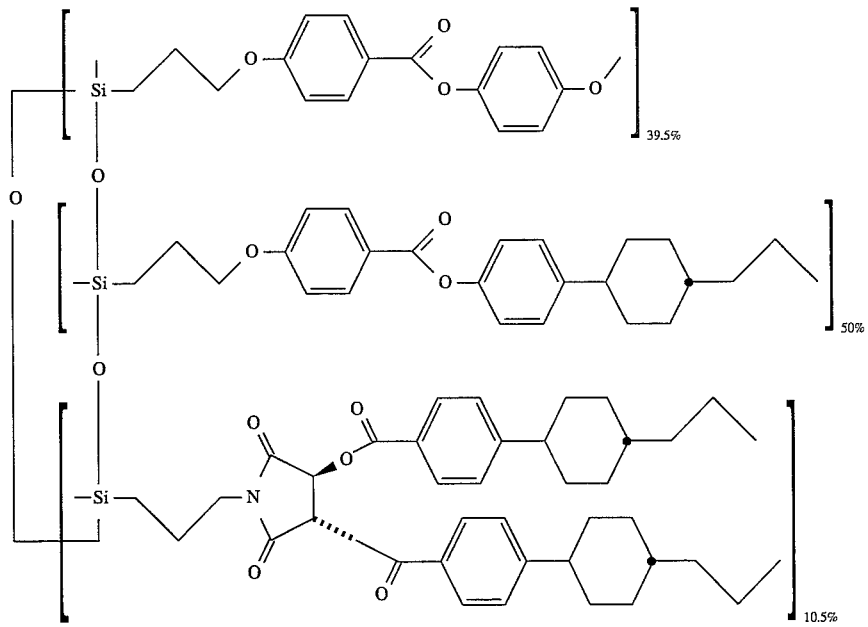

What is claimed is:

1. A liquid-crystalline organosiloxane containing, per molecule, at least one Si—C-bonded, chiral tartarimide radical of the formula $A^5$ are identical or different, saturated or olefinically unsaturated alkyl, alkoxy or cycloalkyl radicals, each having 1 to 16 carbon atoms, cholestane radicals, cholesteryl radicals, halogen atoms, hydrogen atoms, hydroxyl, nitrile, acryloxy, (meth)-acryloxy, (meth)acryloxyethyleneoxy, (meth)acryloxydi-(ethyleneoxy), (meth)acryloxytri(ethyleneoxy), R- or S-tetrahydrofurancarboxylate and trialkylsiloxy groups whose alkyl radicals each have 1 to 8 carbon atoms, a, b, c, d, f, g, h, i and k are each identical or different integers having a value of from 0 to 3, where the sum a+b+c+d+e+f+g+h+i+k is at least 2 and the sum of d and i is at most 4, and e is a number having a value of 0 to 1.

2. A liquid-crystalline organosiloxane as claimed in claim 1, comprising of at least two units of formula

 (3), in which

B is a radical of formula 1, and, optionally, a radical of the formula

 (4), where, in the above formulas 3 and 4,

R are identical or different, substituted or unsubstituted $C_1$- to $C_{18}$-hydrocarbon radicals, o is an integer having a value of from 0 to 3, p is an integer having a value of from 0 to 3 and a mean value of from 0.8 to 2.2, q is an integer having a value of from 0 to 3, and the sum of o, p and q is at most 3, and M, $A^5$ and k are as defined for formula 1.

3. A process for the preparation of a liquid-crystalline organosiloxane as claimed in claim 2, in which n in the radicals of formula 2 is an integer having a value of from 2 to 20, wherein organosiloxanes of the formula

 (14), and/or organosilanes of the formula

 (15), are reacted with compounds of the formula

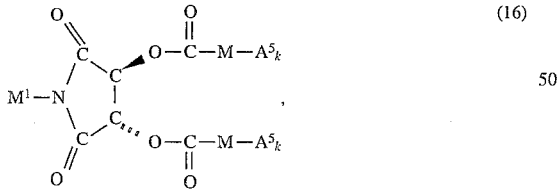 (16)

and, optionally, compounds of the formula

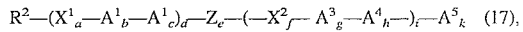 (17), and, with the proviso that if organosilanes of formula 15 are employed, the resultant organosilanes of the formula

 (18), are condensed, where, in the above formulas 14 to 18, $M^1$ is a radical of the formula

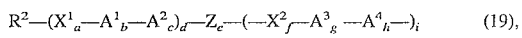 (19),

Y is a condensable group, $R^2$ is a radical of the formula $C_nH_m^1$, in which $m^1$ has the value 2n−1 or 2n−3, and r and s are each an integer having a value of from 0 to 3, the sum of o, r and s is at most 3, and o, p, q, M, $X^1$, $X^2$, $A^1$, $A^2$, $A^3$, $A^4$, $A^5$, a, b, c, d, e, f, g, h, i, k, Z, B and R are as defined in claim 2.

4. A liquid-crystalline organosiloxane as claimed in claim 2, wherein the liquid-crystalline organosiloxane is a mixture of said organosiloxanes containing chiral tartarimides.

5. A liquid-crystalline organosiloxane as claimed in claim 4, further containing liquid-crystalline mixtures of methacryloxy and/or acryloxy groups containing components or pure organosiloxanes containing tartarimide radicals.

6. A compound of the formula

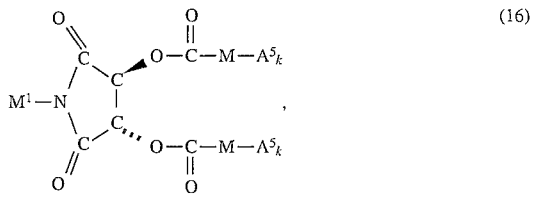 (16)

in which M, $M^1$, $A^5$ and k are as defined in claim 1.

7. An organosilane of the formula

 (18)

in which o is an integer having a value of 1, 2 or 3, n and s are integers having a value of from 0 to 3, R is identical or different, substituted or unsubstituted C1 to C18 hydrocarbon radicals, Y is a group capable of being condensed, and B is a chiral tartarimide radical of formula (1).

* * * * *